US012623982B2

(12) United States Patent
Kolev et al.

(10) Patent No.: US 12,623,982 B2

(45) Date of Patent: May 12, 2026

(54) PROCESS FOR DEHYDRATION OF NORMAL PARAFFINS TO OLEFINS

(71) Applicant: UOP LLC, Des Plaines, IL (US)

(72) Inventors: Evgeny T. Kolev, Arlington Heights, IL (US); Phuong T.M. Do, Mount Prospect, IL (US)

(73) Assignee: UOP LLC, Des Plaines, IL (US)

(*) Notice: Subject to any disclaimer, the term of this patent is extended or adjusted under 35 U.S.C. 154(b) by 129 days.

(21) Appl. No.: 18/500,163

(22) Filed: Nov. 2, 2023

(65) Prior Publication Data

US 2024/0400475 A1 Dec. 5, 2024

Related U.S. Application Data

(60) Provisional application No. 63/504,884, filed on May 30, 2023.

(51) Int. Cl.

| | |
|---|---|
| ***C07C 5/327*** | (2006.01) |
| ***C07C 2/64*** | (2006.01) |
| ***C07C 4/06*** | (2006.01) |
| ***C07C 5/05*** | (2006.01) |
| ***C07C 7/13*** | (2006.01) |

(52) U.S. Cl.

CPC ................ *C07C 5/327* (2013.01); *C07C 2/64* (2013.01); *C07C 4/06* (2013.01); *C07C 5/05* (2013.01); *C07C 7/13* (2013.01)

(58) Field of Classification Search

CPC .. C07C 5/327; C07C 2/64; C07C 4/06; C07C 5/05; C07C 7/13; C07C 7/00

See application file for complete search history.

(56) References Cited

U.S. PATENT DOCUMENTS

| | | | |
|---|---|---|---|
| 4,133,842 | A | 1/1979 | Anderson |
| 6,177,381 | B1 | 1/2001 | Jensen et al. |
| 8,865,956 | B2 | 10/2014 | Anumakonda et al. |
| 9,079,814 | B2 | 7/2015 | Frey et al. |
| 10,894,753 | B1 | 1/2021 | Hickman et al. |

(Continued)

FOREIGN PATENT DOCUMENTS

| | | | |
|---|---|---|---|
| EP | 1966357 | B1 | 4/2019 |
| JP | S5579327 | A | 6/1980 |

(Continued)

OTHER PUBLICATIONS

Extended European Search report from corresponding European application No. EP23211836.4, mailed on Mar. 20, 2024.

(Continued)

*Primary Examiner* — Ali Z Fadhel

(57) ABSTRACT

Processes for dehydrogenating normal paraffins derived from natural oils to olefins are described. The feed stream is passed through an adsorption bed comprising alkaline or alkaline earth cation exchange X-Zeolite to removes essentially all oxygenates and aromatics from the feed stream. One or more additional adsorbent beds having different adsorbents can also be included to remove additional oxygenates and aromatics as well as sulfur compounds, nitrogen compounds, phosphorous compounds, or combinations thereof. The dehydrogenation process can be part of a process for producing alkylbenzenes from natural oils.

17 Claims, 2 Drawing Sheets

(56) References Cited

U.S. PATENT DOCUMENTS

| | | | | |
|---|---|---|---|---|
| 2006/0247481 | A1* | 11/2006 | Kulprathipanja | C07C 2/66 585/520 |
| 2008/0071127 | A1* | 3/2008 | Kulprathipanja | C07C 2/66 585/521 |
| 2008/0194895 | A1 | 8/2008 | Sohn et al. | |
| 2009/0158637 | A1 | 6/2009 | McCall et al. | |
| 2013/0079570 | A1 | 3/2013 | Anumakonda et al. | |
| 2013/0079573 | A1 | 3/2013 | Bozzano et al. | |
| 2013/0253243 | A1 | 9/2013 | Bozzano et al. | |
| 2013/0317267 | A1 | 11/2013 | Anumakonda et al. | |
| 2013/0338410 | A1 | 12/2013 | Wang et al. | |
| 2014/0364355 | A1 | 12/2014 | Frey et al. | |
| 2015/0361012 | A1 | 12/2015 | Sohn et al. | |
| 2016/0068453 | A1 | 3/2016 | Fichtl et al. | |
| 2016/0289139 | A1 | 10/2016 | Baird et al. | |
| 2017/0029347 | A1 | 2/2017 | Ellig et al. | |
| 2018/0179124 | A1 | 6/2018 | Siedler et al. | |
| 2022/0056351 | A1 | 2/2022 | Karvo et al. | |
| 2022/0298425 | A1 | 9/2022 | Rämöet al. | |
| 2024/0400477 | A1 | 12/2024 | Do et al. | |

FOREIGN PATENT DOCUMENTS

| | | | |
|---|---|---|---|
| JP | 2002060760 | A | 2/2002 |
| JP | 2009518534 | A | 5/2009 |
| JP | 2014526552 | A | 10/2014 |
| WO | 2008013519 | A2 | 1/2008 |
| WO | 2014003906 | A1 | 1/2014 |

OTHER PUBLICATIONS

Extended European Search report from European application No. EP23210889.4, mailed on Jun. 3, 2024.

Extended European Search report from European application No. EP23210890.2, mailed on Jun. 3, 2024.

Extended European Search report from European application No. EP23211561.8, mailed on May 10, 2024.

Roald Brosius et al., Selective Formation of Linear Alkanes from n-Hexadecane Primary Hydrocracking in Shape-Selective MFI Zeolites by Competitive Adsorption of Water, ACS Catal. 2016, 6, 7710-7715.

* cited by examiner

PROCESS FOR DEHYDRATION OF NORMAL PARAFFINS TO OLEFINS

RELATED APPLICATIONS

This application claims priority to U.S. Provisional Patent Application Ser. No. 63/504,884, filed on May 30, 2023, the entirety of which is incorporated herein by reference.

BACKGROUND

Linear alkylbenzenes are organic compounds with the formula $C_6H_5C_nH_{2n+1}$. While the alkyl carbon number, "n" can have any practical value, detergent manufacturers desire that alkylbenzenes have alkyl carbon number in the range of 9 to 16 and preferably in the range of 9 to 14. These specific ranges are often required when the alkylbenzenes are used as intermediates in the production of surfactants for detergents. The alkyl carbon number in the range of 9 to 14 falls in line with the specifications of the detergents industry.

Because the surfactants created from alkylbenzenes are biodegradable, the production of alkylbenzenes has grown rapidly since their initial uses in detergent production in the 1960s. The linearity of the paraffin chain in the alkylbenzenes is key to the material's biodegradability and effectiveness as a detergent. A major factor in the final linearity of the alkylbenzenes is the linearity of the paraffin component.

While detergents made utilizing alkylbenzene-based surfactants are biodegradable, previous processes for creating alkylbenzenes are not based on renewable sources. Specifically, alkylbenzenes are currently produced from kerosene refined from crude extracted from the earth. Due to the growing environmental prejudice against fossil fuel extraction and economic concerns over exhausting fossil fuel deposits, there may be support for using an alternate source for biodegradable surfactants in detergents and in other industries.

The C9 to C14 paraffins generated from feedstocks based on vegetable oils or animal fats contain contaminants that can poison dehydrogenation catalysts. The contaminants can also cause discoloration of the linear alkylbenzenes and linear alkylbenzene sulfonates. The contaminants can include aromatics, light oxygenates, fatty acids, fatty esters, and the like. These contaminants need to be removed before the C9 to C14 paraffins are dehydrogenated.

Accordingly, it is desirable to provide decontaminated C9 to C14 paraffins from renewable easily processed triglycerides and fatty acids from vegetable, animal, nut, and/or seed oils to the dehydrogenation unit. Palm kernel oil, coconut oil and babassu oil have a composition that is high in the desirable range of C9-C14 n-paraffins that aligns with the alkyl carbon number range desired of the detergent industry. Such renewable sources also have a high amount of nC16 to nC18 feeds, and it is desirable to convert those feeds to nC9 to nC14 feeds with a high per-pass yield. These nC9 to nC14 intermediate products are useful in eventually making linear alkylbenzene types of detergents through additional process steps. It is further desirable that the resulting nC9 to nC14 paraffins are linear products with a minimum of branched isomer products.

DETAILED DESCRIPTION

Figure 1:
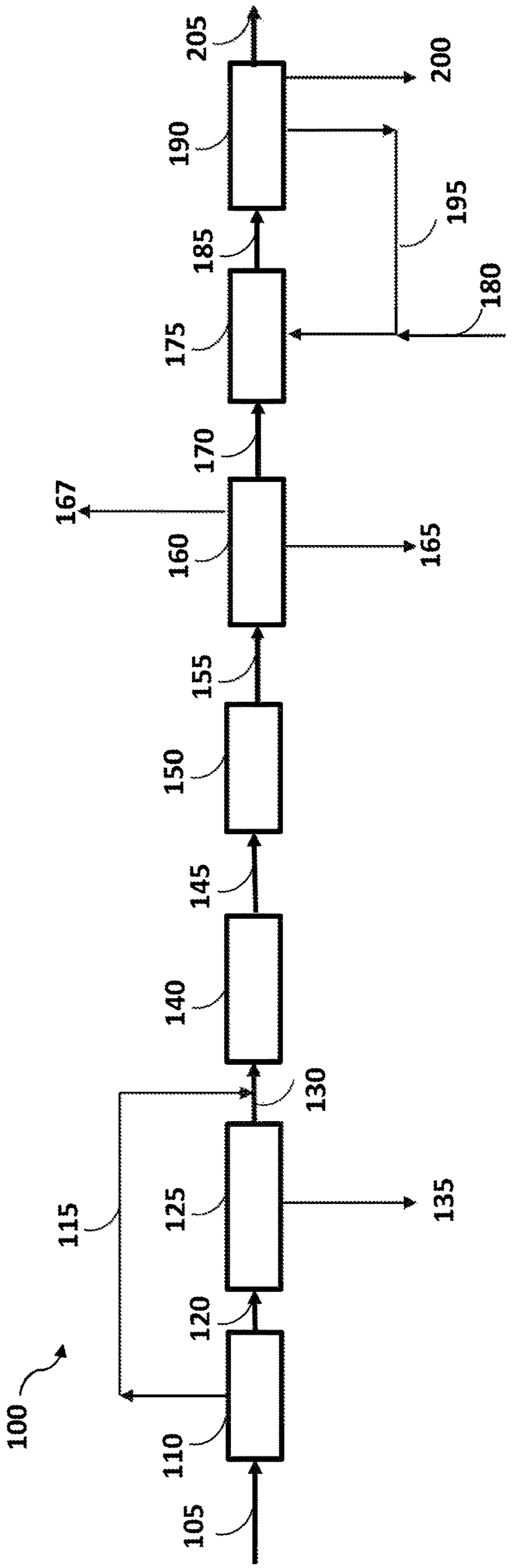
FIG. 1 is a schematic view of one embodiment of a process for producing alkylbenzenes from triglycerides according to the present invention.

The present invention relates to a process for dehydrogenation of normal paraffins to olefins. The paraffins come from renewable feedstocks comprising natural oils, such as vegetable oils, animal fats, nut, and/or seed oils, and triglyceride-containing oils. The purification process for the renewable bio-paraffin stream involves passing the stream through one or more adsorbent beds comprising adsorbents.

Natural oils are not based on kerosene or other fossil fuels. Natural oils include those derived from plant or algal material or animal fats, nut, and/or seed oils, and triglyceride-containing oils, and are often referred to as renewable oils. Natural oils typically comprise triglycerides, free fatty acids, or combinations thereof. Natural oils include, but are not limited to, Arachis oil (peanut oil; groundnut oil), Babassu oil, Coconut oil, Cottonseed oil, Grapeseed oil, Maize oil (corn oil), Mustard seed oil, Palm kernel oil, Palm oil, Palm olein (the liquid fraction derived from the fractionation of palm oil), Palm stearin (the high-melting fraction derived from the fractionation of palm oil), Rapeseed oil, Rapeseed oil-low erucic acid (low erucic acid turnip rape oil; low erucic acid colza oil; canola oil), Safflowerseed oil (safflower oil; carthamus oil; kurdee oil), Safflowerseed oil—high oleic acid (high oleic acid safflower oil; high oleic acid carthamus oil; high oleic acid kurdee oil), Sesameseed oil (sesame oil; gingelly oil; benne oil; ben oil; till oil; tillie oil), Soya bean oil (soybean oil), Sunflowerseed oil (sunflower oil), and Sunflowerseed oil-high oleic acid (high oleic acid sunflower oil).

The feed stream derived from the natural oils comprises normal paraffins, iso paraffins, olefins, oxygenates, and up to 10 wt. % aromatics.

The contaminants in the feed stream may include oxygenates and/or aromatics and/or fatty acids and esters. Alkaline or alkaline earth cation exchange X-Zeolite can be used to remove at least a portion of the oxygenates, aromatics, and fatty acids and esters in the paraffin stream derived from the natural oil. Suitable adsorbents for removing the oxygenates and aromatics include, but are not limited to, alkaline or alkaline earth cation exchange X-Zeolite.

Following contaminant removal, the treated stream comprising no more than 6000 ppm of the aromatics and no more than 100 ppm of the oxygenates.

A second adsorbent bed can optionally be included to further reduce the level of oxygenates, aromatics, and fatty acids and esters in the treated stream. The second adsorbent includes, but is not limited to, 5A zeolite.

The first and/or second adsorbent bed can be regenerated at a predetermined time to remove at least a portion of the oxygenates, or aromatics, or both adsorbed onto the first and/or second adsorbent.

There can be one or more first adsorbent beds and one or more second adsorbent beds.

The paraffin stream from renewable feedstocks comprising vegetable oils and animal fats may also contain other contaminants, such as sulfur compounds, or nitrogen compounds, or phosphorous compounds, or combinations thereof. These contaminants may be removed by passing the treated stream through a third adsorbent bed containing a third adsorbent. The third adsorbent may include, but is not limited to, 13X zeolite, 5A zeolite, an alumina-zeolite, or combinations thereof.

After the feed stream derived from natural oils has passed through the first adsorbent bed, and optionally the second and/or the third adsorbent bed, the treated stream is dehydrogenated to convert at least a portion of the paraffins in the treated stream to olefins. The dehydrogenated stream comprises mono-olefins, di-olefins, and aromatics.

The contaminant removal process can be incorporated into a process for making alkylbenzenes from natural oils. The process involves the deoxygenation of the natural oils to form paraffins. The paraffins are separated (by fractionation or distillation, and the like) into a C9 to C14 stream comprising C9 to C14 paraffins and a C14+ stream comprising C14+ paraffins. The C14+ stream is sent to a separate linear selective cracking unit to crack the C14+ paraffins; the cracked paraffins are fractionated into a first stream comprising the C9 to C14 normal and lightly branched paraffins and a second stream comprising isoparaffins. Contaminants, including but not limited to, oxygenates and/or aromatics and/or fatty acids and ester, and/or sulfur compounds, and/or nitrogen compounds, and/or phosphorous compounds, or combinations thereof, are removed from the C9 to C14 stream and the first stream. The decontaminated stream is dehydrogenated to form olefins, di-olefins, and aromatics. The di-olefins are selectively hydrogenated to form additional olefins, and the aromatics are separated and removed forming an aromatics stream comprising the aromatics and a mono-olefin stream comprising the mono-olefins. Benzene is alkylated with the olefins, and the alkylation effluent comprises alkylbenzenes and benzene. The alkylbenzenes are then isolated.

To limit catalyst deactivation, the feed is treated to remove sulfur contamination before hydrodeoxygenation. Otherwise, sulfur accumulates on the catalyst and leads to deactivation. A high temperature hydrogen treatment was shown to recover some of the lost activity. The degree of hydrodeoxygenation can affect the selectivity to each of the normal paraffins in the 9 to 14 carbon range. A large degree of hydrodeoxygenation can bias the hydrodeoxygenated composition largely in favor of normal dodecane and normal decane to the detriment of normal undecane and normal tridecane. A small degree of hydrodeoxygenation can bias the hydrodeoxygenated composition in favor of normal undecane and normal tridecane to the detriment of normal dodecane and normal decane.

The hydrodeoxygenation reactor temperatures are kept low, less than 343° C. (650° F.) for typical biorenewable feedstocks and less than 304° C. (580° F.) for feedstocks with higher free fatty acid (FFA) concentration to avoid polymerization of olefins found in FFA. Generally, hydrodeoxygenation reactor pressure of about 700 kPa (100 psig) to about 21 MPa (3000 psig) are suitable.

The linearity of the alkylbenzene product is mostly dependent on the linearity of the paraffins used to alkylate the benzene. It is a common rule of thumb by those skilled in the art that the linearity of a paraffin feed drops by about 5-7 mass % after dehydrogenation and alkylation. Therefore, paraffin with 97 mass % linearity (or alternatively 3 mass % isoparaffin) would result in an alkylbenzene product with linearity around 90-92 mass %. This sets the requirement for paraffin linearity about 5-7 mass % higher than the specification for the alkylbenzene product. Typically the linearity of the paraffin product is measured by UOP 621, UOP411, or UOP732 standard test method available from ASTM, which is hereby incorporated by reference in its entirety. Linear alkylbenzenes may be analyzed using ASTM Standard Test Method D4337 hereby incorporated by reference in its entirety.

In the Figure, an exemplary system 100 for producing an alkylbenzene product from a specific triglyceride feed is illustrated.

In the illustrated embodiment, the selected triglyceride feed 105 is delivered to a deoxygenation unit 110 which also receives a hydrogen feed (not shown). In the deoxygenation unit 110, the fatty acids in the selected triglyceride feed 105 are deoxygenated and converted into normal paraffins. Structurally, triglycerides are formed by three, typically different, fatty acid molecules that are bonded together with a glycerol bridge. The glycerol molecule includes three hydroxyl groups (HO—) and each fatty acid molecule has a carboxyl group (COOH). In triglycerides, the hydroxyl groups of the glycerol join the carboxyl groups of the fatty acids to form ester bonds. Therefore, during deoxygenation, the fatty acids are freed from the triglyceride structure and are converted into normal paraffins. The glycerol is converted into propane, and the oxygen in the hydroxyl and carboxyl groups is converted into water, carbon dioxide, or carbon monoxide. The deoxygenation reaction for fatty acids and triglycerides are respectively illustrated as:

$$H_2 + R—COOH \longrightarrow R + H_2O + CO_2$$

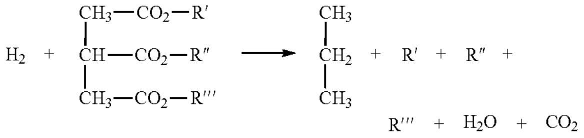

During the deoxygenation reaction, the length of a paraffin chain R″ created will vary by a value of one depending on the exact reaction pathway. It is understood that deoxygenation includes at least one of hydrodeoxygenation, decarboxylation, and decarbonylation, or any combination thereof. For instance, if carbon dioxide is formed, then the chain will have one fewer carbon than the fatty acid source. If water is formed, then the chain will match the length of the fatty acid source.

Operating conditions for the deoxygenating unit include pressures in the range of from about 250 to about 800 psig (about 1724 to about 5516 kPa) and temperatures in the range of from about 274° C. to about 371° C. (about 525° F. to about 700° F.) in one embodiment, from about 274° C. to about 338° C. (about 525° F. to about 640° F.) in another embodiment and from about 274° C. to about 310° C. (about 525° F. to about 590° F.) in another embodiment. Catalysts may include those containing one or more of Ni, Mo, Co, P, such as Ni—Mo, Ni—Mo—P, Ni—Co—Mo, or Co—Mo, on aluminas, silica, titania, zirconia, and mixtures thereof. Suitable hydrogen to hydrocarbon mole ratios include from about 1500 to 10,000, from about 4000 to 9000, and from about 5000-8000 standard cubic feet per barrel of feedstock (scf/B). Suitable space velocities include 0.2-3.0 $hr^{-1}$ LHSV. Conditions are selected to minimize cracking or isomerizing the paraffins.

The deoxygenated product containing normal paraffins, water, carbon dioxide, carbon monoxide, and propane is fractionated into a C9 to C14 stream 115 and a C14+ stream 120. The separation may be performed in a multi-stage fractionation unit, distillation system or similar known apparatus. In any event, the separator removes the water, carbon dioxide, carbon monoxide, and propane from the deoxygenated product. A naphtha stream of paraffins with carbon chain lengths of $C_5$ to $C_9$ (not shown) may also be formed.

The C14+ stream 120 is sent to the linear selective cracking unit 125 where it is selectively cracked to form a first stream 130 comprising normal or lightly branched C9 to C14 paraffins and a second stream 135 comprising isoparaffins The linear selective cracking takes place in a separate unit, rather than in the bottom bed of a first stage hydrocracking reactor because sulfur and nitrogen contaminants from the first stage can poison a metal-based hydrocracking catalyst. The C14+ paraffins are selectively cracked over the C9 to C14 due to higher absorption energy.

Selection of particular metal catalysts, including noble metals (such as ruthenium and platinum), and nickel can produce a much higher yield of normal paraffins with 9-14 carbons than previous processes. Suitable catalysts include, but are not limited to, $Ru/ZrO_2$, a Pt—$Al_2O_3$, Ni-alumina, or a NiOx/clay. With these catalysts, the C14+ stream is able to generate linear cracking products without significant amounts of branched isomer production.

Of the preferred catalysts, the Ru catalyst exhibits much higher activity and per-pass nC9 to nC14 yield than the other catalysts. Under the optimized reaction conditions, it also produces very small amounts of methane and isomerized product. This has been found to be the best catalyst for such chemical transformation process. The Pt—Al2O3 catalyst can produce even lower methane yield than the Ru based catalyst with slightly less linear product yield.

The C9 to C14 stream 115 from the deoxygenation unit 110 and the first stream 130 from the linear selective cracking unit 125 are sent to a decontamination unit 140 as described above. The decontamination unit 140 removes contaminants from the C9 to C14 paraffins in the C9 to C14 stream 115 and the first stream 130. The contaminants include, but are not limited to, oxygenates and/or aromatics and/or fatty acids and ester, and/or sulfur compounds, and/or nitrogen compounds, and/or phosphorous compounds, or combinations thereof.

The decontaminated stream 145 is sent to a dehydrogenation unit 150 where hydrogen is removed to produce a dehydrogenated stream 155 comprising mono-olefins, di-olefins, and aromatics. In the dehydrogenation unit 150, the paraffins are dehydrogenated into mono-olefins of the same carbon numbers as the paraffins. Typically, dehydrogenation occurs through known catalytic processes, such as the commercially popular Pacol process. Di-olefins (i.e., dienes) and aromatics are also produced as an undesired result of the dehydrogenation reactions as expressed in the following equations:

$C_xH_{2x+2} \rightarrow C_xH_{2x} + H_2$ Mono-olefin formation:

$C_xH_{2x} \rightarrow C_xH_{2x-2} + H_2$ Di-olefin formation:

$C_xH_{2x-2} \rightarrow CH_{2x-6} + 2H_2$ Aromatic formation:

Operating conditions for the dehydrogenation unit 150 include space velocities from about 5 to about 50 LHSV and from about 20 to about 32 LHSV; pressures from about 34 kPa (g) to about 345 kPa (g) (about 5 psig to about 50 psig) and from about 103 kPa (g) to about 172 kPa (g) (about 15 psig to about 25 psig); temperatures from about 400° C. to about 500° C. and from about 440° C. to about 490° C., and hydrogen to hydrocarbon mole ratios from about 1-12 and from about 3-7. An example of a suitable catalyst is a Pt on alumina catalyst where platinum is attenuated with an attenuator metal. Another suitable catalyst is described in U.S. Pat. No. 6,177,381 hereby incorporated by reference in its entirety. The dehydrogenation unit 150 may be operated dry or with water injection up to about 2000 mass-ppm water. Hydrogen can be recycled to the deoxygenation unit upstream.

The dehydrogenated stream 155 is sent to a selective hydrogenation unit 160, such as a DeFine reactor, where at least a portion of the di-olefins are hydrogenated to form additional mono-olefins. As a result, the mono-olefin stream 170 has an increased mono-olefin concentration compared to the dehydrogenated stream 155. The aromatics are separated and removed as aromatics stream 165. A light end stream 167 containing any lights, such as butane, propane, ethane and methane, that resulted from cracking or other reactions during upstream processing can also be removed if needed.

The mono-olefin stream 170 comprising mono-olefins is sent to the alkylation unit 175 along with a benzene stream 180. The benzene is alkylated with the mono-olefins to form alkylbenzene. The alkylation unit 175 contains a catalyst, such as a solid acid catalyst, that supports alkylation of the benzene with the mono-olefins. Fluorinated silica-alumina, hydrogen fluoride (HF), aluminum chloride ($AlCl_3$), zeolitic, and ionic liquid catalysts are examples of major catalysts in commercial use for the alkylation of benzene with linear mono-olefins and may be used in the alkylation unit 175. As a result of alkylation, alkylbenzene, typically called linear alkylbenzene (LAB), is formed according to the reaction:

$$C_6H_6 + C_xH_{2x} \rightarrow C_6H_5C_xH_{2x+1}$$

Suitable operating conditions for the alkylation unit 175 include space velocities from 1 to about 10 LHSV, pressures to maintain liquid phase operation, such as about 2068 kPa (g) to about 4137 kPa (g) (about 300 psig to about 600 psig), temperatures in the range of from about 80° C. to about 180° C. and 120° C. to about 170° C., benzene to olefin mole ratios of about 3 to about 40 and about 8 to about 35.

Surplus amounts of benzene are supplied to the alkylation unit 175 to achieve high degree of desired alkylation. Therefore, the alkylation effluent 185 exiting the alkylation unit 175 contains alkylbenzene and unreacted benzene. Further the alkylation effluent 185 may also include some unreacted paraffins. The alkylation effluent 185 is passed to a benzene separation unit 190, such as a fractionation column, for separating the unreacted benzene and paraffins from the alkylation effluent 185. The unreacted benzene exits the benzene separation unit 190 in a benzene recycle stream 195 that may be sent back into the alkylation unit 175 to maintain the desired benzene/olefin ratio (e.g., 1-50) to reduce the volume of fresh benzene needed. The fresh benzene requirement (i.e., the net benzene) is determined by the net olefin to the alkylation unit. A paraffin stream 200 can also be separated out and recycled to the dehydrogenation unit 150.

As a result of the post-alkylation separation processes, the linear alkylbenzene product 205 is isolated. It is noted that such separation processes are not necessary in all embodiments in order to isolate the linear alkylbenzene product 205.

The linear alkylbenzene product 205 is a linear alkylbenzene product comprising: alkylbenzenes having the formula $C_6H_5C_nH_{2n-1}$ wherein n is from 9 to 14. In some embodiments, at least 80 mass % of the alkylbenzenes have linear alkyl groups, or at least 90 mass %.

The linear alkylbenzene may be sulfonated to provide a linear alkylbenzene sulfonate product comprising: alkylbenzene sulfonate compounds having the formula $C_nH_{2n+1}C_6H_4SO_3H$ wherein n is from 10 to 14, or wherein n is from 11 to 13.

The term "column" means a distillation column or columns for separating one or more components of different volatilities. Unless otherwise indicated, each column includes a condenser on an overhead of the column to condense and reflux a portion of an overhead stream back to the top of the column and a reboiler at a bottom of the column to vaporize and send a portion of a bottoms stream back to the bottom of the column. Feeds to the columns may be preheated. The top pressure is the pressure of the overhead vapor at the vapor outlet of the column. The bottom temperature is the liquid bottom outlet temperature. Unless indicated otherwise, overhead lines and bottoms lines refer to the net lines from the column downstream of any reflux or reboil take-off to the column. Stripper columns may omit a reboiler at a bottom of the column and instead provide heating requirements and separation impetus from a fluidized inert media such as steam.

As used herein, the term "a component-rich stream" or "a component stream" means that the stream coming out of a vessel has a greater concentration of the component than the feed to the vessel. As used herein, the term "a component-lean stream" means that the lean stream coming out of a vessel has a smaller concentration of the component than the feed to the vessel.

EXAMPLES

Example 1

A coconut oil feed was deoxygenated, to form paraffins, dehydrogenated to form mono-olefins, and benzene was alkylated with the mono-olefins to form an alkylbenzene product with a modern carbon content of 62 mass 96 modern carbon as determined by ASTM D6866 as compared to a theoretical modern carbon content of 66.4 mass %, a bromine number of 1 g Br/per gram sample as determined by UOP standard test method 304, and a linearity of 92 mass %.

Example 2

Figure 2:
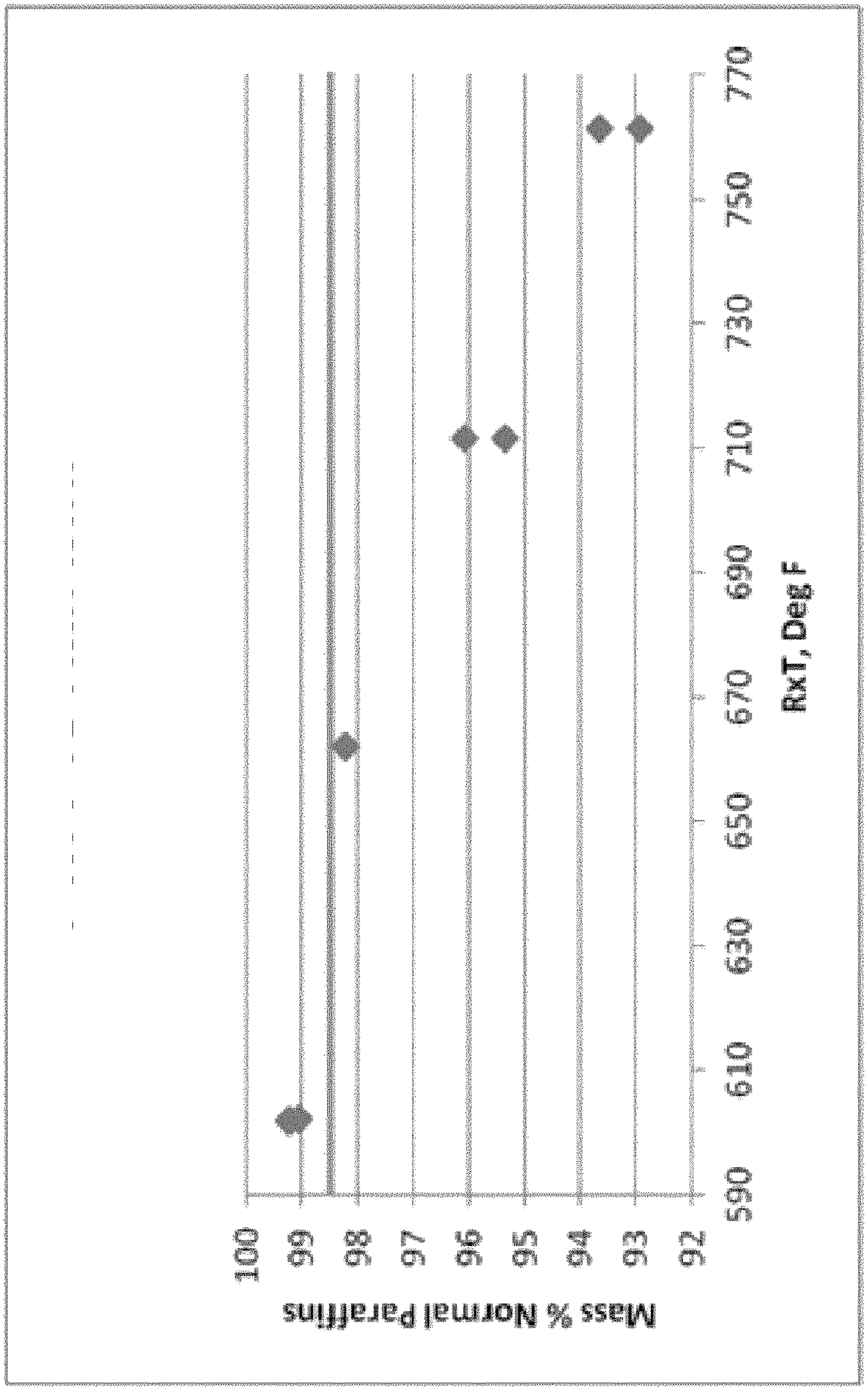
FIG. 2 is a plot of the mass-% normal paraffins versus deoxygenation temperature in accordance with Example 2.

An oil was deoxygenated using a catalyst at a pressure of 480 psig, H, to bio-oil ratio of 7200 scf/B and a LHSV of 1 hr'. During operation, the deoxygenation reaction temperature was increased in steps from 315° C. (600° F.) to 34.9° C. (660° F.) and then to 377° C. (710° F.) and 404° C. (760° F.) to monitor the response of linearity in the final product to reaction temperature. The results are shown in FIG. 2 which is a plot of the concentration in mass % of normal C10-C13 paraffins versus reaction temperature. FIG. 2 clearly demonstrates that as the deoxygenation reaction temperature is increased, the concentration of linear paraffins decreases. Controlling the temperature to less than 404° C. (760° F.) resulted in greater than 92 mass percent linear paraffins.

Note: Examples 1 and 2 were previously included in U.S. Pat. No. 9,079,814 as Examples 3 and 4.

Specific Embodiments

While the following is described in conjunction with specific embodiments, it will be understood that this description is intended to illustrate and not limit the scope of the preceding description and the appended claims.

A first embodiment of the invention is a method for dehydrogenation of normal paraffins to olefins comprising passing a feed stream derived from natural oils comprising C9 to C14 normal paraffins, iso paraffins, olefins, oxygenates, and up to 10 wt. % aromatics through a first adsorbent bed containing a first adsorbent comprising alkaline or alkaline earth cation exchange X-Zeolite wherein the adsorbent removes at least a portion of the oxygenates and aromatics from the paraffin stream by adsorption to form a treated stream; and dehydrogenating the treated stream to convert at least a portion of the treated stream to olefins and provide a dehydrogenated stream comprising mono-olefins, di-olefins, and aromatics. An embodiment of the invention is one, any or all of prior embodiments in this paragraph up through the first embodiment in this paragraph further comprising regenerating the adsorbent bed at a predetermined time to remove at least a portion of the oxygenates, or aromatics, or both adsorbed onto the adsorbent. An embodiment of the invention is one, any or all of prior embodiments in this paragraph up through the first embodiment in this paragraph further comprising; passing the treated stream though a second adsorbent bed containing a second adsorbent comprising 5A zeolite to remove additional oxygenates and aromatics to form a second treated stream. An embodiment of the invention is one, any or all of prior embodiments in this paragraph up through the first embodiment in this paragraph further comprising regenerating the second adsorbent bed at a predetermined time to remove at least a portion of the oxygenates, or aromatics, or both adsorbed onto the second adsorbent. An embodiment of the invention is one, any or all of prior embodiments in this paragraph up through the first embodiment in this paragraph wherein the feed stream is formed by deoxygenating a natural oil to form a paraffin stream comprising C9 to C28 paraffins; linear selective cracking the paraffin stream in a linear selective cracking unit under linear selective cracking conditions in the presence of a linear selective cracking catalyst to form a first stream comprising normal or lightly branched C9 to C14 paraffins and a second stream comprising isoparaffins. An embodiment of the invention is one, any or all of prior embodiments in this paragraph up through the first embodiment in this paragraph further comprising removing contaminants from the treated stream in a third adsorbent bed comprising a third adsorbent to form a decontaminated stream wherein the contaminates comprise sulfur compounds, or nitrogen compounds, or phosphorous compounds, or combinations thereof, wherein the third adsorbent comprises 13X zeolite, 5A zeolite, an alumina-zeolite, or combinations thereof before dehydrogenating the treated stream. 7 An embodiment of the invention is one, any or all of prior embodiments in this paragraph up through the first embodiment in this paragraph further comprising selectively hydrogenating the di-olefins in the dehydrogenated stream to form additional mono-olefins, and separating and removing the aromatics from the mono-olefins to form an aromatics stream comprising the aromatics and a mono-olefins stream comprising the mono-olefins alkylating benzene with the mono-olefins under alkylation conditions to provide an alkylation effluent comprising alkylbenzenes and benzene; isolating the alkylbenzenes to provide the alkylbenzene product derived from the natural oil. An embodiment of the invention is one, any or all of prior embodiments in this paragraph up through the first embodiment in this paragraph wherein the treated stream comprises no more than 6000 ppm of the aromatics and no more than 100 ppm of the oxygenates.

A second embodiment of the invention is a method for dehydrogenation of normal paraffins to olefins comprising passing a feed stream comprising normal paraffins, iso paraffins, olefins, up to 10 wt. % aromatics, and oxygenates through an adsorbent bed containing an adsorbent comprising alkaline or alkaline earth cation exchange X-Zeolite wherein the adsorbent removes at least a portion of the oxygenates and the aromatics from the paraffin stream by adsorption to form a treated stream; removing contaminants from the treated stream in a third adsorbent bed comprising a third adsorbent to form a decontaminated stream wherein the contaminates comprise sulfur compounds, or nitrogen compounds, or phosphorous compounds, or combinations thereof, wherein the adsorbent comprises 13X zeolite, 5A zeolite, an alumina-zeolite, or combinations thereof; and dehydrogenating the decontaminated stream to convert at least a portion of the decontaminated stream to olefins and provide a dehydrogenated stream comprising mono-olefins, di-olefins, and aromatics; regenerating the adsorbent bed at a predetermined time to remove at least a portion of the oxygenates, or aromatics, or both adsorbed onto the adsorbent. An embodiment of the invention is one, any or all of prior embodiments in this paragraph up through the second embodiment in this paragraph further comprising; passing the treated stream though a second adsorbent bed containing a second adsorbent comprising 5A zeolite to remove additional oxygenates and aromatics to form a second treated stream before removing the contaminants in the third adsorbent bed. An embodiment of the invention is one, any or all of prior embodiments in this paragraph up through the second embodiment in this paragraph further comprising regenerating the second adsorbent bed at a predetermined time to remove at least a portion of the oxygenates, or aromatics, or both adsorbed onto the second adsorbent. An embodiment of the invention is one, any or all of prior embodiments in this paragraph up through the second embodiment in this paragraph wherein the feed stream is formed by deoxygenating a natural oil to form a paraffin stream comprising C9 to C28 paraffins; linear selective cracking the paraffin stream in a linear selective cracking unit under linear selective cracking conditions in the presence of a linear selective cracking catalyst to form a first stream comprising normal or lightly branched C9 to C14 paraffins and a second stream comprising isoparaffins. An embodiment of the invention is one, any or all of prior embodiments in this paragraph up through the second embodiment in this paragraph further comprising selectively hydrogenating the di-olefins in the dehydrogenated stream to form additional mono-olefins, and separating and removing the aromatics from the mono-olefins to form an aromatics stream comprising the aromatics and a mono-olefins stream comprising the mono-olefins alkylating benzene with the mono-olefins under alkylation conditions to provide an alkylation effluent comprising alkylbenzenes and benzene; isolating the alkylbenzenes to provide the alkylbenzene product derived from the natural oil. An embodiment of the invention is one, any or all of prior embodiments in this paragraph up through the second embodiment in this paragraph wherein the treated stream comprises no more than 6000 ppm of the aromatics and no more than 100 ppm of the oxygenates.

A third embodiment of the invention is a method for dehydrogenation of normal paraffins to olefins comprising deoxygenating a natural oil to form a paraffin stream comprising C9 to C28 paraffins; linear selective cracking the paraffin stream in a linear selective cracking unit under linear selective cracking conditions in the presence of a linear selective cracking catalyst to form a first stream comprising normal or lightly branched C9 to C14 paraffins and a second stream comprising isoparaffins; passing the first stream comprising normal paraffins, iso paraffins, olefins, oxygenates, and up to 10 wt. % aromatics, through a first adsorbent bed containing a first adsorbent comprising alkaline or alkaline earth cation exchange X-Zeolite wherein the adsorbent removes at least a portion of the oxygenates and the aromatics from the first stream by adsorption to form a treated stream; removing contaminants from the treated stream in a third adsorbent bed before dehydrogenating the treated stream, the third adsorbent bed comprising a third adsorbent to form a decontaminated stream wherein the contaminants comprise sulfur compounds, or nitrogen compounds, or phosphorous compounds, or combinations thereof, wherein the third adsorbent comprises 13X zeolite, 5A zeolite, an alumina-zeolite, or combinations thereof. dehydrogenating the decontaminated stream to convert at least a portion of the decontaminated stream to olefins and provide a dehydrogenated stream comprising mono-olefins, di-olefins, and aromatics; selectively hydrogenating the di-olefins in the dehydrogenated stream to form additional mono-olefins, and separating and removing the aromatics from the mono-olefins to form an aromatics stream comprising the aromatics and a mono-olefins stream comprising the mono-olefins alkylating benzene with the mono-olefins under alkylation conditions to provide an alkylation effluent comprising alkylbenzenes and benzene; and isolating the alkylbenzenes to provide the alkylbenzene product derived from the natural oil. An embodiment of the invention is one, any or all of prior embodiments in this paragraph up through the third embodiment in this paragraph further comprising; regenerating the first adsorbent bed at a predetermined time to remove at least a portion of the oxygenates, or aromatics, or both adsorbed onto the first adsorbent. An embodiment of the invention is one, any or all of prior embodiments in this paragraph up through the third embodiment in this paragraph further comprising; passing the treated stream though a second adsorbent bed containing a second adsorbent comprising 5A zeolite to remove additional oxygenates and aromatics to form a second treated stream. An embodiment of the invention is one, any or all of prior embodiments in this paragraph up through the third embodiment in this paragraph further comprising; regenerating the second adsorbent bed at a predetermined time to remove at least a portion of the oxygenates, or aromatics, or both adsorbed onto the second adsorbent. An embodiment of the invention is one, any or all of prior embodiments in this paragraph up through the third embodiment in this paragraph wherein the treated stream comprises no more than 6000 ppm of the aromatics and no more than 100 ppm of the oxygenates.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

What is claimed is:

1. A method for dehydrogenation of normal paraffins to olefins comprising:

deoxygenating a natural oil to form a feed stream comprising C9 to C28 paraffins;

linear selective cracking the feed stream in a linear selective cracking unit under linear selective cracking conditions in the presence of a linear selective cracking catalyst to form a first stream comprising normal or lightly branched C9 to C14 paraffins and a second stream comprising isoparaffins;

passing said first stream through a first adsorbent bed containing a first adsorbent comprising alkaline or alkaline earth cation exchange X-Zeolite wherein the adsorbent removes at least a portion of the oxygenates and aromatics from the first stream by adsorption to form a treated stream; and dehydrogenating the treated stream to convert at least a portion of the treated stream to olefins and provide a dehydrogenated stream comprising mono-olefins, di-olefins, and aromatics.

2. The method of claim 1 further comprising:

regenerating the adsorbent bed at a predetermined time to remove at least a portion of the oxygenates, or aromatics, or both adsorbed onto the adsorbent.

3. The method of claim 1 further comprising;

passing the treated stream though a second adsorbent bed containing a second adsorbent comprising 5A zeolite to remove additional oxygenates and aromatics to form a second treated stream.

4. The method of claim 3 further comprising:

regenerating the second adsorbent bed at a predetermined time to remove at least a portion of the oxygenates, or aromatics, or both adsorbed onto the second adsorbent.

5. The method of claim 1 further comprising:

removing contaminants from the treated stream in a third adsorbent bed comprising a third adsorbent to form a decontaminated stream wherein the contaminates comprise sulfur compounds, or nitrogen compounds, or phosphorous compounds, or combinations thereof, wherein the third adsorbent comprises 13X zeolite, 5A zeolite, an alumina-zeolite, or combinations thereof before dehydrogenating the treated stream.

6. The method of claim 1 further comprising:

selectively hydrogenating the di-olefins in the dehydrogenated stream to form additional mono-olefins, and separating and removing the aromatics from the mono-olefins to form an aromatics stream comprising the aromatics and a mono-olefins stream comprising the mono-olefins:

alkylating benzene with the mono-olefins under alkylation conditions to provide an alkylation effluent comprising alkylbenzenes and benzene; and isolating the alkylbenzenes to provide the alkylbenzene product derived from the natural oil.

7. The method of claim 1 wherein the treated stream comprises no more than 6000 ppm of the aromatics and no more than 100 ppm of the oxygenates.

8. A method for dehydrogenation of normal paraffins to olefins comprising:

deoxygenating a natural oil to form a feed stream comprising C9 to C28 paraffins, linear selective cracking the feed stream in a linear selective cracking unit under linear selective cracking conditions in the presence of a linear selective cracking catalyst to form a first stream comprising normal or lightly branched C9 to C14 paraffins and a second stream comprising isoparaffins;

passing said first stream through an adsorbent bed containing an adsorbent comprising alkaline or alkaline earth cation exchange X-Zeolite wherein the adsorbent removes at least a portion of the oxygenates and the aromatics from the first stream by adsorption to form a treated stream;

removing contaminants from the treated stream in a third adsorbent bed comprising a third adsorbent to form a decontaminated stream wherein the contaminates comprise sulfur compounds, or nitrogen compounds, or phosphorous compounds, or combinations thereof, wherein the adsorbent comprises 13X zeolite, 5A zeolite, an alumina-zeolite, or combinations thereof; and dehydrogenating the decontaminated stream to convert at least a portion of the decontaminated stream to olefins and provide a dehydrogenated stream comprising mono-olefins, di-olefins, and aromatics; and regenerating the adsorbent bed at a predetermined time to remove at least a portion of the oxygenates, or aromatics, or both adsorbed onto the adsorbent.

9. The method of claim 8 further comprising;

passing the treated stream though a second adsorbent bed containing a second adsorbent comprising 5A zeolite to remove additional oxygenates and aromatics to form a second treated stream before removing the contaminants in the third adsorbent bed.

10. The method of claim 8 further comprising:

regenerating the second adsorbent bed at a predetermined time to remove at least a portion of the oxygenates, or aromatics, or both adsorbed onto the second adsorbent.

11. The method of claim 8 further comprising:

selectively hydrogenating the di-olefins in the dehydrogenated stream to form additional mono-olefins, and separating and removing the aromatics from the mono-olefins to form an aromatics stream comprising the aromatics and a mono-olefins stream comprising the mono-olefins:

alkylating benzene with the mono-olefins under alkylation conditions to provide an alkylation effluent comprising alkylbenzenes and benzene; and isolating the alkylbenzenes to provide the alkylbenzene product derived from the natural oil.

12. The method of claim 8 wherein the treated stream comprises no more than 6000 ppm of the aromatics and no more than 100 ppm of the oxygenates.

13. A method for dehydrogenation of normal paraffins to olefins comprising:

deoxygenating a natural oil to form a first stream comprising C9 to C28 paraffins;

linear selective cracking the first stream in a linear selective cracking unit under linear selective cracking conditions in the presence of a linear selective cracking catalyst to form a first stream comprising normal or lightly branched C9 to C14 paraffins and a second stream comprising isoparaffins;

passing the first stream comprising normal paraffins, iso paraffins, olefins, oxygenates, and up to 10 wt. % aromatics, through a first adsorbent bed containing a first adsorbent comprising alkaline or alkaline earth cation exchange X-Zeolite wherein the adsorbent removes at least a portion of the oxygenates and the aromatics from the first stream by adsorption to form a treated stream;

removing contaminants from the treated stream in a third adsorbent bed before dehydrogenating the treated stream, the third adsorbent bed comprising a third adsorbent to form a decontaminated stream wherein the contaminants comprise sulfur compounds, or nitrogen compounds, or phosphorous compounds, or combinations thereof, wherein the third adsorbent comprises 13X zeolite, 5A zeolite, an alumina-zeolite, or combinations thereof;

dehydrogenating the decontaminated stream to convert at least a portion of the decontaminated stream to olefins and provide a dehydrogenated stream comprising mono-olefins, di-olefins, and aromatics;

selectively hydrogenating the di-olefins in the dehydrogenated stream to form additional mono-olefins, and separating and removing the aromatics from the mono-olefins to form an aromatics stream comprising the aromatics and a mono-olefins stream comprising the mono-olefins;

alkylating benzene with the mono-olefins under alkylation conditions to provide an alkylation effluent comprising alkylbenzenes and benzene; and isolating the alkylbenzenes to provide the alkylbenzene product derived from the natural oil.

14. The method of claim 13 further comprising;

regenerating the first adsorbent bed at a predetermined time to remove at least a portion of the oxygenates, or aromatics, or both adsorbed onto the first adsorbent.

15. The method of claim 13 further comprising;

passing the treated stream though a second adsorbent bed containing a second adsorbent comprising 5A zeolite to remove additional oxygenates and aromatics to form a second treated stream.

16. The method of claim 15 further comprising;

regenerating the second adsorbent bed at a predetermined time to remove at least a portion of the oxygenates, or aromatics, or both adsorbed onto the second adsorbent.

17. The method of claim 13 wherein the treated stream comprises no more than 6000 ppm of the aromatics and no more than 100 ppm of the oxygenates.

* * * * *